US006316258B1

(12) United States Patent
Noble et al.

(10) Patent No.: US 6,316,258 B1
(45) Date of Patent: Nov. 13, 2001

(54) METHODS FOR PREVENTING AND TREATING FIBROTIC DISEASES RESULTING FROM ACCUMULATION OF EXCESS EXTRACELLULAR MATRIX INDUCED BY TGFβ USING RENIN INHIBITORS

(75) Inventors: Nancy A. Noble; Wayne A. Border, both of Salt Lake City, UT (US)

(73) Assignee: University of Utah, Salt Lake City, UT (US)

( * ) Notice: Subject to any disclaimer, the term of this patent is extended or adjusted under 35 U.S.C. 154(b) by 0 days.

(21) Appl. No.: 09/211,916

(22) Filed: Dec. 15, 1998

Related U.S. Application Data

(63) Continuation-in-part of application No. 09/005,255, filed on Jan. 9, 1998, now abandoned.

(51) Int. Cl.[7] .................................................. G01N 33/50

(52) U.S. Cl. ............................................ 435/375; 435/7.1

(58) Field of Search ....................... 514/44, 12; 536/24.3, 536/23.1, 24.5; 435/375, 325, 7.1, 91.1

(56) References Cited

U.S. PATENT DOCUMENTS 5,821,227 * 10/1998 Dennis et al. ......................... 514/12

OTHER PUBLICATIONS

Andrea D. Branch, A good antisense molecule is hard to find, TIBS, 47–48, Feb. 1998.*
Eugene Uhlmann and Anusch Peyman, Antisense Oligonucleotides: A new Therapeutic Principle, Chemical Reviews, pp. 545–546, Jun. 1990.*
Stanley T. Crooke, Basic Principles of Antisense Therapeutics, Springer–Verlag, NY, p. 3, Jul. 1998.*
Antonipillai, T. et al., "Transforming Growth Factor–β is a Renin Secretagogue at Picomolar Concentrations," *American Journal of Physiology*, Oct. 1993, 265(4):F537–41. (Exhibit 1).
Arnheim, Norman and Erlich, Henry, "Polymerase Chain Reaction Strategy," *Annual Review of Biochemistry*, 1992, 61:131–56. (Exhibit 2).
Arai, Makoto et al., "In Vivo Transfection of Genes for Renin and Angiotensinogen into the Glomerular Cells Induced Phenotypic Change of the Mesangial Cells and Glomerular Sclerosis," *Biochemical and Biophysical Research Communications*, Jan. 17, 1995, 206(2):525–32. (Exhibit 3).
Bagchus, W.M. et al., "Glomerulonephritis Induced by Monoclonal Anti–Thy 1.1 Antibodies," *Laboratory Investigation*, Dec. 1986, 55(6):680–7. (Exhibit 4).
Badasso, M. et al., "Crystallization and Preliminary X–ray Analysis of Complexes of Peptide Inhibitors with Human Recombinant and Mouse Submandibular Renins," *Journal of Molecular Biology*, 1992, 223:447–53. (Exhibit 5).

Baricos, William H. et al., "ECM Degradation by Cultured Human Mesangial Cells is Mediated by a PA/plasmin/MMP–2 Cascade," *Kidney International*, 1995, 47:1039–47. (Exhibit 6).
Bennett, C. Frank et al., "Cationic Lipids Enhance Cellular Uptake and Activity of Phosphorothioate Antisense Oligonucleotides," *Molecular Pharmacology An International Journal*, Jun. 1992, 41(6):1023–33. (Exhibit 7).
Boutorine, A.S. and E.V. Kostina, "Reversible Covalent Attachment of Cholesterol to Oligodeoxyribonucleotides for Studies of the Mechanisms of their Penetration Into Eucaryotic Cells," *Biochimie*, 1993, 75(1–2):35–41. (Exhibit 8).
Bongartz, Jean–Pierre et al., "Improved Biological Activity of Antisense Oligonucleotides Conjugated to a Fusogenic Peptides," *Nucleic Acid Research*, Nov. 11, 1994, 22(22):4681–8. (Exhibit 9).
Border, Wayne A. and Nancy A. Noble, "Transforming Growth Factor β In Tissue Fibrosis," *The New England Journal of Medicine*, Nov. 10, 1994, 33(119):1286–92 (Exhibit 10).
Border, Wayne A. et al., "Suppression of Experimental Glomerulonephritis by Antiserum Against Transforming Growth Factor β1, " *Nature*, Jul. 1990, 346:371–4. (Exhibit 11).
Border, Wayne A. et al., "Natural Inhibitor of Transforming Growth Factor–β Protects Against Scarring in Experimental Kidney Disease," *Nature*, Nov. 1992, 360:361–4. (Exhibit 12).
Campbell, Duncan J. and Anthony J. Valentijn, "Identification of Vascular Renin–Binding Proteins by Chemical Cross–Linking: Inhibition of Binding of Renin by Renin Inhibitors," *Journal of Hypertension*, Aug. 1994, 12(8):879–90. (Exhibit 13).
Capaccioli, Sergio et al., "Cationic Lipids Improve Antisense Oligonucleotide Uptake and Prevent Degradation in Cultured Cells and in Human Serum," *Buochemical and Biophysical Research Communications*, Dec. 15, 1993, 197(2):818–25. (Exhibit 14).
Chansel, Dominique et al., "Identification and Regulation of Renin in Human Cultured Mesangial Cells," *American Journal of Physiology*, Jan. 1987, 252(1):F32–8. (Exhibit 15).
Cote, Richard J. et al., "Generation of Human Monoclonal Antibodies Reactive With Cellular Antigens," *Proc. Natl. Acad. Sci. USA*, Apr. 1983, 80:2026–30. (Exhibit 16).
Compagnon, B. et al., "Targeting of Poly(rI)–Poly(rC) by Fusogenic (F Protein) Immunoliposomes," *Experimental Cell Research*, 1992, 200:333–8. (Exhibit 17).

(List continued on next page.)

Primary Examiner—John L. LeGuyader
Assistant Examiner—Janet Epps
(74) *Attorney, Agent, or Firm*—Mandel & Adriano

(57) ABSTRACT

The present invention is methods for inhibiting the renin-induced production of TGFβ using a renin inhibitory agent to reduce excess accumulation of extracellular matrix in tissue in a subject, and to the use of renin inhibitory agents and additional TGFβ inhibitory agents to reduce TGFβ production to treat and prevent fibrotic diseases.

9 Claims, 5 Drawing Sheets

OTHER PUBLICATIONS

Dhanaraj, V. et al., "X–ray Analyses of Peptide–Inhibitor Complexes Define the Structural Basis of Specificity for Human and Mouse Renins," *Nature*, Jun. 1992, 357(6377):466–72. (Exhibit 18).

Dodson, Mark et al., "Specialized Nucleoprotein Sturctures at the Origin or Replication of Bacteriophage λ: Localized Unwinding of Duplex DNA by a Six–Protein Reaction," *Proc. Natl. Acad. Sci. USA,* Oct. 1986, 83:7638–42. (Exhibit 19).

Dostal, David E. et al., "An Improved Method for Absolute Quantification of mRNA Using Multiplex Polymerase Chain Reaction: Determination of Renin and Angiotensinogen mRNA Levels in Various Tissues," *Analytical Biochemistry,* 1994, 223:239–50. (Exhibit 20).

Dzau, Victor J. and Jeffrey Kreisberg, "Cultured Glomerular Mesangial Cells Contain Renin: Influence of Calcium and Isoproterenol," *Journal of Cardiovascular Pharmacology,* 1986, 8(Supp. 10):S6–10. (Exhibit 21).

Eltayeb, B.O. et al., "Effects of Captopril on Serum Levels of TGF–β1 in Insulin–Dependent Diabetic Patients," *Journal of the American Society of Nephrology,* Sep. 1997, 8:110A. (Exhibit 22).

Felgner, P.L et al., "Cationic Liposome Mediated Transfection," *Proceedings of the Western Pharmacology Society,* 1989, 32:115–21. (Exhibit 23).

Felgner, Philip L. et al., "Lipofection: A Highly Efficient, Lipid–Mediated DNA–transfection Procedure (Liposomes/Cationic Lipid Vesicles/Gene Transfer)," *Proc. Acad. Natl. Sci. USA,* Nov. 1987, 84:7413–7. (Exhibit 24).

Fischli, Walter et al., "Ro 42–5892 Is a Potent Orally Active Renin Inhibitor in Primates," *Hypertension,* Jul. 1991, 18(1):22–31. (Exhibit 25).

Galen, F.X. et al., "New Monoclonal Antibodies Directed Against Human Renin Powerful Tools for the Investigation of the Renin System," *The Journal of Clinical Investigation,* Sep. 1984, 74(3):723–35. (Exhibit 26).

Gibbons, Gary H. et al., "Vascular Smooth Muscle Cell Hypertrophy vs. Hyperplasia Autocrine Transforming Growth factor–β, Expression Determines Growth Response to Angiotensin II, " *The Journal of Clinical Investigation,* Aug. 1992, 90(2):456–61. (Exhibit 27).

Greene, E.L. et al., "Role of Aldosterone in the Remnant Kidney Model in the Rat," *The Journal of Clinical Investigation,* Aug. 1996, 98(4):1063–8. (Exhibit 28).

Horikoshi, Satoshi et al., "Water Deprivation Stimulates Transforming Growth Factor–62 2 Accumulation in the Juxtaglomerular Apparatus of Mouse Kidney," *The Journal of Clinical Investigation,* Dec. 1991, 88:2117–22. (Exhibit 30).

Husted, Russelll F. et al., "Induction of Resistance to Mineralocorticoid Hormone in Cultured Inner Medullary Collecting Duct Cells by TGF–β1," *American Journal of Physiology,* Nov. 1994, 267(5):F767–75. (Exhibit 31).

Isaka, Yoshitaka et al., "Gene Therapy by Skeletal Muscle Expression of Decorin Prevents Fibrotic Disease in Rat Kidney," *Nature Medicine,* Apr. 1996, 2(4):418–23. (Exhibit 32).

Isaka, Yoshitaka et al., "Glomerulosclerosis Induced by In Vivo Transfection of Transforming Growth Factor–β or Platelet–derived Growth Factor Gene into the Rat Kidney," *The Journal of Clinical Investigation,* Dec. 1993, 92:2597–2601. (Exhibit 33).

Johnson, Richard J. et al, "The Activated Mesangial Cell: A Glomerular "Myofibrolast"?, " *Journal of the American Society of Nephrology,* 1992, 2(2):S190–7. (Exhibit 34).

Kagami, Shoji et al., "Coordinated Expression of β1 Integrins and Transforming Growth Factor–β–Induced Matrix Proteins in Glomerulonephritis," *Laboratory Investigation,* Jul. 1993, 69(1):68–76. (Exhibit 35).

Kashgarian, Michael and R. Bernd Sterzel,"The Pathbiology of Mesangium," *Kidney Intenational,* 1992, 41:524–9. (Exhibit 36).

Kitamura, Masanori et al., "Transfer of a Mutated Gene Encoding Active Transforming Growth Factor–1 Suppresses Mitogenesis and IL–1 Response in the Glomerulus," *Kidney International,* 1995, 48:1747–57 (Exhibit 37).

Klahr, Saulo et al., "The Progression of Renal Disease," *The New England Journal of Medicine,* 1988, 318(25):1657–66. (Exhibit 38).

Kohler, G. and C. Milstein, "Continuous Cultures of Fused Cells Secreting Antibody of Predefined Specificity," *Nature,* Aug. 1975, 256(5517):495–7. (Exhibit 39).

Kozbor, Danuta and John C. Roder, "The Production of Monoclonal Antibodies From Human Lymphocytes," *Immunology Today,* 1983, 4:72–9. (Exhibit 40).

Leonetti, Jean–Paul et al., "Antibody–Targeted Liposomes Containing Oligodeoxyribonucleotides Complmentary to Viral RNA Selectivity Inhibit Viral Replication," *Proc. Natl., Acad. Sci. USA,* Apr. 1990, 87:2448–51. (Exhibit 41).

Mathews, Salima et al., "Recombinant Human Renin Produced in Different Expression Systems Biochemical Properties and 3D Structure," *Protein Expression and Purification,* Feb. 1996, 7(1):81–91. (Exhibit 41).

Mann, Ricahrd et al, "Construction of a Retrovirus Packaging Mutant and Its Use to Produce Helper–Free Defective Retrovirus," *Cell,* 1983, 33:153–9. (Exhibit 43).

Miller, A. Dusty and Carol Buttimore, "Redesign of Retrovirus Packaging Cell Lines to Avoid Recombination Leading to Helper Virus Production," *Molecular and Cellular Biology,* Aug. 1986, 6(8):2895–2902. (Exhibit 44).

Morishita, Ryuichi et al, "Single Intraluminal Delivery of Antisense CDC2 Kinase and Proliferating–Cell Nuclear Antigen Oligonucleotides Results In Chronic Inhibition of Neointimal Hyperplasia," *Proc. Natl. Acad. Sci. USA,* Sep. 1993, 90:8474–8. (Exhibit 45).

Nguyen, Genevieve et al., "Specific Receptor Binding of Renin on Human Mesangial Cells in Culture Increases Plasminogen Activator Inhibitor–1 Antigen," *Kidney International,* 1996, 50:1897–1903 (Exhibit 46).

Noble, Nancy A. and Wayne A. Border, "Angiostenin II in Renal Fibrosis: Should TGF–β Rather Than Blood Pressure Be The Therapeutic Target?" *Seminars in Nephrology,* Sep. 1997, 17(5):455–66. (Exhibit 47).

Okuda, Seiya et al, "Elevated Expression of Transforming Growth Factor–62 and Proteoglycan Production in Experimental Glomerulonephritis Possible Role in Expansion of the Mesangial Extracellular Matrix," *Journal of Clinical Investigation,* Aug. 1990, 86:453–62. (Exhibit 48).

Peten, Emmanuel P. et al., "The Contribution of Increased Collagen Synthesis to Human Glomeruloosclerosis: A Quantitative Analysis of α2IV Collagen mRNA Expression by Competitive Polymerase Chain Reaction," *The Journal of Experimental Medicine,* Dec. 1992, 176:1571–6. (Exhibit 49).

Ray, Patricio E. et al., "Renal Vascular Induction of TGF-β2 and Renin By Potassium Depletion," *Kidney International,* 1993, 44:1006–13. (Exhibit 50).

Ray Patricio E. et al., "Modulation of Renin Release and Renal Vascular Smooth Muscle Cell Contractility by TGF-β2," *Progression of Chronic Renal Disease,* Koide, H. and I. Ichikawa, eds., 1996, 118:238–48. (Exhibit 51).

Rahuel, Joseph et al., "The Crystal Structures of Recombinant Glycosylated Human Renin Alone and in Complex with a Transition State Analog Inhibitor," *Journal of Structural Biology,* 1991, 107:227–36.

Rajaonarivony, M et al., "Development of a New Drug Carrier Made From Alginate," *Journal of Pharmaceutical Sciences,* Sep. 1993, 82(9):912–7. (Exhibit 53).

Sealey, Jean F. et al., "Specific Prorenin/Renin Binding (ProBP) Identification and Characterization of a Novel Membrane Site," *American Journal of Hypertension,* May 1996, 9(5):491–502. (Exhibit 54).

Sielecki, Anita R. et al., "Structure of Recombinant Human Renin, A Target For Cardiovascular–Active Drugs, at 2.5 Å Resolution," *Science,* Mar. 1989, 243:1346–51. (Exhibit 55).

Tomooka, Suguru et al., "Glomerular Matrix Accumulation is Linked to Inhibition of the Plasmin Protease System," *Kidney International,* 1992, 42:1462–9. (Exhibit 56).

Uotila, Marjatta et al., "Two–Site Sandwhich Enzyme Immunoassay with Monoclonal Antibodies To Human Alpha–Fetoprotein," *Journal of Immunological Methods,* 1981, 42:11–5. (Exhibit 57).

Véneiant, Murielle et al., "Vascular Damage Without Hypertension In Transgenic Rats Expressing Prorenin Exclusively in the Liver," *The Journal of Clinical Investigation,* Nov. 1996, 98(9):1966–70. (Exhibit 58).

Vlahos, Chris J. et al., "The Purification and Characterization of Recombinant Human Renin Expressed in the Human Kidney Cell Line 293," *Biochemical and Biophysical Research Communications,* Aug. 1990, 171(1):375–83. (Exhibit 59).

Wagner, Richard W., "Gene Inhibition Using Antisense Oligodeoxynucleotides," *Nature,* Nov. 1994, 372:333–5. (Exhibit 60).

Wagner, Richard W. et al., "Antisense Gene Inhibition by Oligonucleotides Containing C–5 Propyne Pyrimidines," *Science,* Jun. 1993, 260:1510–3. (Exhibit 61).

Wexler, Ruth R. et al., "Rationale for the Chemical Development of Angiotensin II Receptor Antagonists," *American Journal of Hypertension,* 1992, 5:209S–20S. (Exhibit 62).

Zhu, Ning et al., "Systemic Gene Expression After Intravenous DNA Delivery Into Adult Mice," *Science,* Jul. 1993, 261:209–11. (Exhibit 63).

* cited by examiner

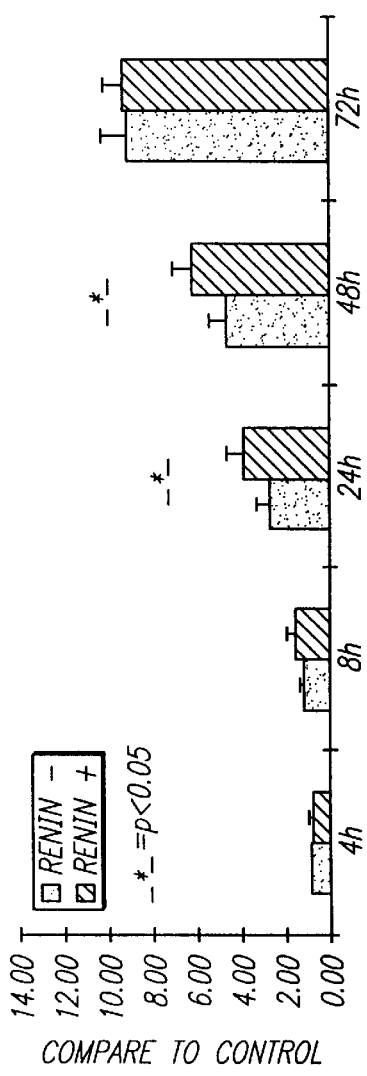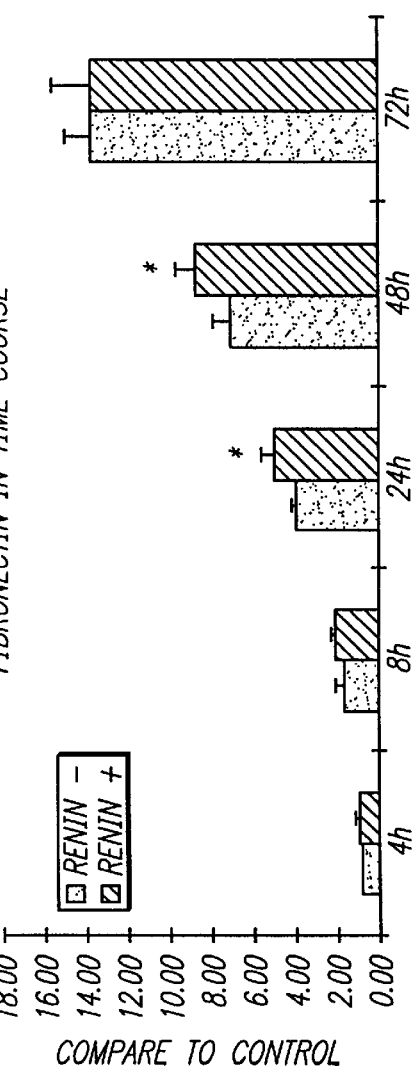

METHODS FOR PREVENTING AND TREATING FIBROTIC DISEASES RESULTING FROM ACCUMULATION OF EXCESS EXTRACELLULAR MATRIX INDUCED BY TGFβ USING RENIN INHIBITORS

RELATED APPLICATIONS

This application is a Continuation-in-part application of U.S. Ser. No. 09/005,255, filed Jan. 9, 1998, now abandoned the contents of which are hereby incorporated by reference in their entirety.

FIELD OF THE INVENTION

This invention relates to a method for reducing accumulation of excess extracellular matrix induced by TGFβ in a subject by inhibiting renin, and more particularly to the prevention and treatment of fibrotic disease resulting from accumulation of excess extracellular matrix using renin inhibitory agents and compositions including renin inhibitory agents and TGFβ inhibitory agents.

BACKGROUND OF THE INVENTION

Overproduction of transforming growth factor (TGF)β clearly underlies tissue fibrosis caused by excess deposition of extracellular matrix resulting in disease. TGFβ's fibrogenic action results from simultaneous stimulation of matrix protein synthesis, inhibition of matrix degradation and enhanced integrin expression that facilitates extracellular matrix (ECM) assembly. Overproduction of TGFβ has been demonstrated in glomerulonephritis, diabetic nephropathy and hypertensive glomerular injury. Suppression of the production of ECM and prevention of accumulation of mesangial matrix in glomeruli of glomerulonephritic rats has been demonstrated by intravenous administration of neutralizing antibodies specific for TGFβ (Border et al., Nature 346:371–374 (1990)) or administration of purified decorin (Border et al., Nature 360:361–364 (1992)) and by introduction of nucleic acid encoding decorin, a TGFβ-inhibitory agent, into a rat acute mesangial model of glomerulonephritis (Isaka et al., Nature Med. 2:418–423 (1996)).

Renin is an aspartyl proteinase synthesized by juxtaglomerular kidney cells and mesangial cells in humans and rats. (Chansel et al., Am. J. Physiol. 252:F32–F38 (1987) and Dzau and Kreisberg, J. Cardiovasc. Pharmacol. 8(Suppl 10):S6–S10 (1986)). Renin plays a key role in the regulation of blood pressure and salt balance. Its major source in humans is the kidney where it is initially produced as preprorenin. Signal peptide processing and glycosylation are followed by secretion of prorenin and its enzymatically active form, mature renin. The active enzyme triggers a proteolytic cascade by cleaving angiotensinogen to generate angiotensin I, which is in turn converted to the vasoactive hormone angiotensin II by angiotensin converting enzyme ("ACE").

The sequence of the human renin gene is known (GenBank entry M26901). Recombinant human renin has been synthesized and expressed in various expression systems (Sielecki et al., Science 243:1346–1351 (1988), Mathews et al., Protein Expression and Purification 7:81–91 (1996)). Inhibitors of renin are known (Rahuel et al., J. Struct. Biol. 107:227–236 (1991); Badasso et al., J. Mol. Biol. 223:447–453 (1992); and Dhanaraj et al., Nature 357:466–472 (1992)) including an orally active renin inhibitor in primates, Ro 42-5892 (Fischli et al., Hypertension 18:22–31 (1991)). Renin-binding proteins and a cell surface renin receptor on human mesangial cells have been identified (Campbell and Valentijn, J. Hypertens. 12:879–890 (1994), Nguyen et al., Kidney Internat. 50:1897–1903 (1996) and Sealey et al., Amer. J. Hyper. 9:491–502 (1996)).

The renin-angiotensin system (RAS) is a prototypical systemic endocrine network whose actions in the kidney and adrenal glands regulate blood pressure, intravascular volume and electrolyte balance. In contrast, TGFβ is considered to be a typical cytokine, a peptide signaling molecule whose multiple actions on cells are mediated in a local or paracrine manner. Recent data however, indicate that there is an intact RAS in many tissues whose actions are entirely paracrine and TGFβ has wide-ranging systemic (endocrine) effects. Moreover, RAS and TGFβ act at various points to regulate the actions of one another.

In a systemic response to an injury such as a wound, the RAS rapidly generates AII that acts by vasoconstriction to maintain blood pressure and later stimulates the secretion of aldosterone, resulting in an increase in intravascular volume. In the wound, TGFβ is rapidly released by degranulating platelets and causes a number of effects including: 1) autoinduction of the production of TGFβ by local cells to amplify biological effects; 2) chemoattraction of monocyte/macrophages that debride and sterilize the wound and fibroblasts that begin synthesis of ECM; 3) causing deposition of new ECM by simultaneously stimulating the synthesis of new ECM, inhibiting the proteases that degrade matrix and modulating the numbers of integrin receptors to facilitate cell adhesion to the newly assembled matrix; 4) suppressing the proinflammatory effects of interleukin-1 and tumor necrosis factor; 5) regulating the action of platelet derived growth factor and fibroblast growth factor so that cell proliferation and angiogenesis are coordinated with matrix deposition; and 6) terminating the process when repair is complete and the wound is closed (Border and Noble, Scientific Amer. Sci. & Med. 2:68–77 (1995)).

Interactions between RAS and TGFβ occur at both the systemic and molecular level. It has been shown that TGFβ's action in causing ECM deposition in a healing wound is the same action that makes TGFβ a powerful fibrogenic cytokine. (Border and Noble, New Engl. J. Med. 331:1286–1292 (1994); and Border and Ruoslahti, J. Clin. Invest. 90:107(1992)). Indeed, it is the failure to terminate the production of TGFβ that distinguishes normal tissue repair from fibrotic disease. RAS and TGFβ co-regulate each other's expression. Thus, both systems may remain active long after an emergency response has been terminated, which can lead to progressive fibrosis. The kidney is particularly susceptible to overexpression of TGFβ. The interrelationship of RAS and TGFβ may explain the susceptibility of the kidney to TGFβ overexpression and why pharmacologic suppression of RAS or inhibition of TGFβ are both therapeutic in fibrotic diseases of the kidney. (Noble and Border, Sem. Nephrol., supra and Border and Noble, Kidney Int. 51:1388–1396 (1997)).

Activation of RAS and generation of angiotensin II (AII) are known to play a role in the pathogenesis of hypertension and renal and cardiac fibrosis. TGFβ has been shown to be a powerful fibrogenic cytokine, acting simultaneously to stimulate the synthesis of ECM, inhibit the action of proteases that degrade ECM and increasing the expression of cell surface integrins that interact with matrix components. Through these effects, TGFβ rapidly causes the deposition of excess ECM. AII infusion strongly stimulates the production and activation of TGFβ in the kidney. (Kagami et al., J. Clin. Invest. 93:2431–2437 (1994)). Angiotensin II also upregulates TGFβ production and increases activation when added to cultured vascular smooth muscle cells (Gibbons et al, J. Clin. Invest. 90:456–461 (1992)) and this increase is independent of pressure (Kagami et al., supra). Blockade of AII reduces TGFβ overexpression in kidney and heart, and it is thought that TGFβ mediates renal and cardiacfibrosis associated with activation of RAS (Noble and Border, Sem. Nephrol. 17(5):455–466 (1997)). Blockade of AII using inhibitors of ACE slow the progression of renal fibrotic disease (see, e.g., Anderson et al., J. Clin. Invest. 76:612–619 (1985) and Noble and Border, Sem. Nephrol. 17(5):455–466 (1997)). What is not clear is whether angiotensin blockade reduces fibrosis solely through controlling glomerular hypertension and thereby glomerular injury, or whether pressure-independent as well as pressure-dependent mechanisms are operating. While ACE inhibitors have been shown to slow the progress of fibrotic diseases, they do not halt disease and TGFβ levels remain somewhat elevated.

Thus, RAS and TGFβ can be viewed as powerful effector molecules that interact to preserve systemic and tissue homeostasis. The response to an emergency is that RAS and TGFβ become activated. Continued activation may result in chronic hypertension and progressive tissue fibrosis leading to organ failure. Because of the interplay between the RAS and TGFβ, and the effects of this interplay on tissue homeostasis, blockade of the RAS may be suboptimal to prevent or treat progressive fibrotic diseases such as diabetic nephropathy.

Components of the renin-angiotensin system act to further stimulate production of TGFβ and plasminogen activator inhibitor leading to rapid ECM accumulation. The protective effect of inhibition of the renin-angiotensin system in experimental and human kidney diseases correlates with the suppression of TGFβ production.

The renin molecule has been shown to enzymatically cleave angiotensinogen into Angiotensin I. The angiotensin I is then converted by Angiotensin Converting Enzyme ("ACE") to Angiotensin II which acts as an active metabolite and induces TGFβ production. Angiotensin II is an important modulator of systemic blood pressure. It has been thought that if you decrease hypertension by blocking AII's vasoconstrictor effects fibrotic disease is reduced.

In the glomerular endothelium, activation of RAS and TGFβ have been shown to play a role in the pathogenesis of glomerulonephritis and hypertensive injury. Volume (water) depletion and restriction of potassium have been shown to stimulate both production of renin and TGFβ in the juxtaglomerular apparatus (JGA) of the kidney (Horikoshi et al., J. Clin. Invest. 88:2117–2122 (1992) and Ray et al., Kidney Int. 44:1006–1013 (1993)). ACE inhibitor has also been shown to increase the production of renin and TGFβ, suggesting that AII is not inducing TGFβ but that production of renin and TGFβ are co-regulated. TGFβ has been shown to stimulate the release of renin from kidney cortical slices and cultured JG cells (Antonipillai et al., Am. J. Physiol. 265:F537–F541 (1993); Ray et al., Contrib. Nephrol. 118:238–248 (1996) and Veniant et al., J. Clin. Invest. 98:1996-19970 (1996)). Other interactions between RAS and TGFβ include that AII induces the production of TGFβ in cultured cells and in vivo (Kagami et al., supra). It is thus likely that the fibrogenic effects that have been attributed to AII are actually mediated by TGFβ.

Another interplay between RAS and TGFβ is with the production of aldosterone. Aldosterone overproduction has been linked to hypertension and glomerulosclerosis. AII stimulates the production and release of aldosterone from the adrenal gland. In contrast, TGFβ suppresses aldosterone production and blocks the ability of AII to stimulate aldosterone by reducing the number of AII receptors expressed in the adrenal (Gupta et al., Endocrinol. 131:631–636 (1992)), and blocks the effects of aldosterone on sodium reabsorption in cultured collecting renal duct cells (Husted et al., Am. J. Physiol. Renal, Fluid Electrolyte Physiol. 267:F767–F775 (1994)). Aldosterone may have fibrogenic effects independent of AII, and may upregulate TGFβ expression. The mechanism of aldosterone's pathological effects is unknown but might be due to stimulation of TGFβ production in the kidney (Greene et al., J. Clin. Invest. 98:1063–1068 (1996)).

Prorenin or renin may have AII-independent actions to increase fibrotic disease. Prorenin overexpressing rats were found to be normotensive but to develop severe glomerulosclerosis (Veniant et al., J. Clin. Invest. 98:1996–1970 (1996)). Human recombinant renin added to human mesangial cells induces marked upregulation of production of plasminogen activator inhibitors (e.g. PAI-1) which block the generation of plasmin, a fibrinolytic enzyme important in the dissolution of clots after wounding-PAI-1 is increased in response to added TGFβ (Tomooka et al., Kidney Int. 42:1462–1469 (1992)), which is independent of AII and acts through a renin receptor on mesangial cells, independent of the enzymatic site used to convert angiotensin to angiotensinogen (Nguyen et al., Kidney Int. 50:1897–1903 (1996)). It has been suggested that TGFβ enhances renin release (Antonipillai et al., Am. J. Physiol. 265:F537–F541 (1993) and Ray et al., Contrib. Nephrol. 118:238–248 (1996)).

Thus, the interactions of RAS and TGFβ production form a complex system which impacts fibrotic ECM accumulation and the incidence of fibrotic disease. Various RAS components such as aldosterone, prorenin and renin may be connected with TGFβ production and fibrotic ECM accumulation. Any successful therapeutic regime must take into account these complex relationships to optimize inhibition of TGFβ to prevent and/or reduce ECM accumulation.

In fibrotic diseases overproduction of TGFβ results in accumulation of excess extracellular matrix which leads to tissue fibrosis and eventually organ failure. Accumulation of mesangial matrix is a histological indication of progressive glomerular diseases that lead to glomerulosclerosis and end-stage kidney disease (Klahr et al., N. Engl. J. Med. 318:1657–1666 (1988); Kashgarian and Sterzel, Kidney Int. 41:524–529 (1992)). Rats injected with antithymocyte serum are an accepted model of human glomerulonephritis and this model has demonstrated that overproduction of glomerular TGFβ can underlie the development of glomerulosclerosis (Okuda et al., J. Clin. Invest. 86:453–462 (1990); Border et al., Nature (Lond.) 346:371–374 (1990); Kagami et al., Lab. Invest. 69:68–76 (1993); and Isaka et al., J. Clin. Invest. 92:2597–2602 (1993)). Using cultured rat mesangial cells where the effects of Angiotensin II on glomerular pressure are not a factor, Angiotensin II has been shown to induce TGFβ production and secretion by mesangial cells, and this in turn has been shown to stimulate extracellular matrix production and deposition (Kagami et al., J. Clin. Invest. 93:2431–2437 (1994)). Increases in PAI-1 levels result in decreased degradation of extracellular matrix (Baricos et al., Kidney Int. 47:1039–1047 (1995)). Increases in TGFβ result in increased PAI-1 levels (Tomooka et al., Kidney Int. 42:1462–1469 (1992)). It has been demonstrated that decreasing TGFβ overexpression in a rat model of glomerulonephritis by in vivo injection of neutralizing antibodies to TGFβ, reduces TGFβ overexpression (Border et al., Nature 346:371–374 (1990)), and reduces PAI-1 deposition into the pathological matrix (Tamooka et al., Kidney Int. 42:1462–1469 (1992)). Therefore, decreases in TGFβ levels should result in decreased PAI-1 levels and increased degradation of extracellular matrix to ameliorate organ impairment and fibrotic disease.

It is thus the aim of therapeutic strategies for fibrotic diseases to halt the overproduction of TGFβ and thus reduce the excess accumulation of extracellular matrix in tissues before organ failure occurs. There is a need for improved therapies that take into account the multiple pathways that stimulate TGFβ production.

SUMMARY OF THE INVENTION

Accordingly, the present invention provides methods for inhibiting the renin-induced production of TGFβ by inhibiting renin using renin inhibitory agents including anti-renin antibodies, small molecule antagonists of renin and ligands for the renin receptor. The methods are also for preventing and treating fibrotic disease resulting from the TGFβ-induced accumulation of excess extracellular matrix using a renin inhibitor or compositions containing a renin inhibitory agent and TGFβ inhibitory agents to reduce the production of TGFβ in tissue to prevent organ impairment. The inhibitory agents may be administered as inhibitory compounds in pharmaceutical formulations or as nucleic acid encoding the inhibitors delivered to suitable host cells. The nucleic acid may be directly introduced into a cell in vivo, for example into muscle tissue, or may be first introduced into a cell ex vivo to obtain a cell expressing the inhibitory agent, and the cell then transplanted or grafted into a subject to prevent accumulation of excess extracellular matrix.

BRIEF DESCRIPTION OF THE DRAWINGS

FIGS. 4A and 4B are bar graphs showing time courses of TGFβ (FIG. 4A) and Fn production (FIG. 4B) as described in Example IV, infra.

DETAILED DESCRIPTION OF THE INVENTION

Figure 1:
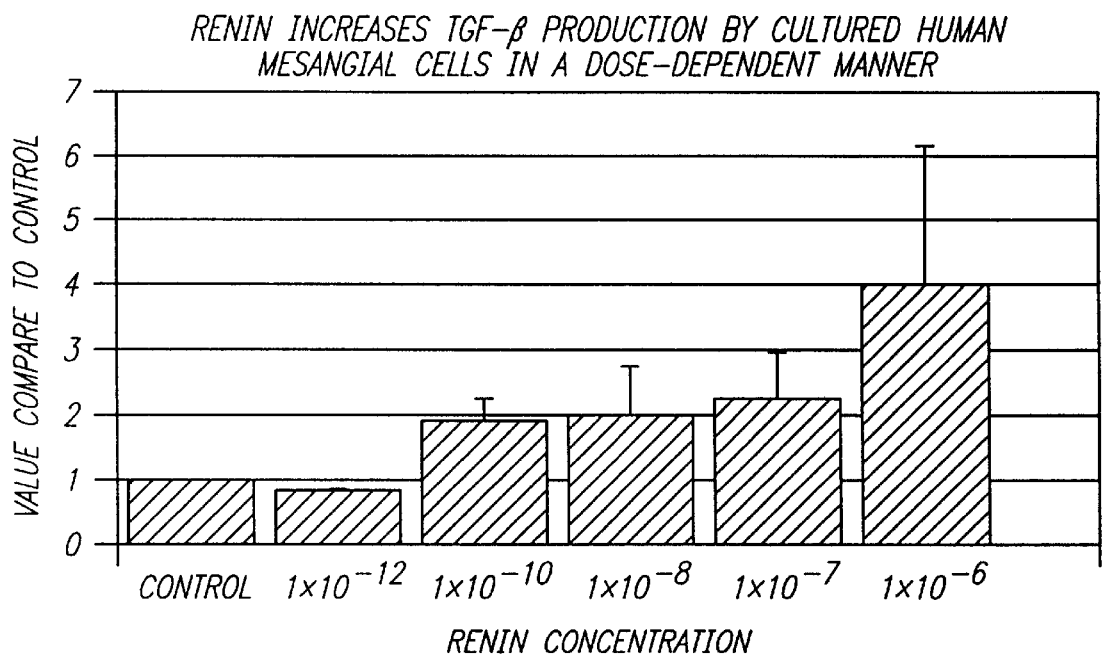
FIG. 1 is a bar graph showing increases in TGFβ production by cultured human mesangial cells in response to renin, as described in Example I, infra.

The present invention is based on the surprising discovery that renin stimulates TGFβ production in cells capable of producing TGFβ, in an angiotensin II and blood pressure independent manner. Therefore, successful therapy and prevention of fibrotic diseases must take into account the multiple pathways of TGFβ production to effectively combat overproduction of TGFβ that results in accumulation of excess extracellular matrix causing organ impairment and ultimately organ failure. Without such multifactorial strategy, inhibition of one pathway of TGFβ production may be insufficient to block accumulation of extracellular matrix and can even result in an increase in the levels of TGFβ production by stimulation of one of the alternative pathways for its production.

The methods of the invention can be used to prevent or treat fibrotic disease in human subjects by inhibiting TGFβ production and the consequent excess accumulation of extracellular matrix in tissues in the subject using renin inhibitory agents and by administering combinations of renin inhibitory and TGFβ inhibitory agents.

The methods of the invention include blocking alternative pathways of TGFβ production, including inhibiting renin using a renin inhibitory agent to reduce accumulation of excess extracellular matrix (ECM). The methods are useful to reduce accumulation of extracellular matrix and prevent fibrotic disease in a subject that results from accumulation of excess ECM.

In one embodiment, a renin inhibitory agent is administered to a subject at high risk for fibrotic disease, such as a person having or at high risk for diabetes, high blood pressure, autoimmune disease (e.g. lupus) and inflammatory diseases. Such high-risk individuals can be scanned using known medical procedures such as tissue biopsies of kidney, lung or liver to determine whether ECM is accumulating. If the agent is renin-specific, it binds to circulating renin and prevents TGFβ overproduction in tissues where ECM is accumulating, such as kidney, lung or liver tissue. If the agent indirectly inhibits renin it reduces the amount of renin produced.

As used herein a "renin inhibitory agent" is an agent that directly or indirectly inhibits renin binding to its receptors, such as a renin-specific inhibitory agent or an agent that blocks an alternative pathway of renin production. For example, an indirect inhibitor would inhibit the synthesis or secretion of renin or sequester it away from its target cells. A renin inhibitory agent also includes inhibitors of the renin precursors preprorenin and prorenin.

As used herein, a "renin-specific inhibitory agent" means a protein or protein fragment containing renin inhibiting activity, including agents that bind directly to renin or are a ligand for renin which prevent it from binding to its receptors. Such agents include renin receptors, and soluble forms and fragments thereof having renin-binding activity, antibodies and antibody fragments specific for renin, and new renin antagonists developed using well known methods for drug discovery as described herein and in the art. A renin-specific inhibiting agent also includes a nucleic acid encoding a particular renin-specific inhibitory agent such as a cDNA, genomic DNA or an RNA or DNA encoding renin-specific inhibitory activity such as a renin antisense oligonucleotide.

In another embodiment, nucleic acid encoding the renin inhibitory agent is introduced into cells in the subject to permit the agent to be expressed and secreted for contacting renin and reducing the production of TGFβ. The nucleic acid may be introduced in a suitable delivery vehicle such as an expression vector or encapsulation unit such as a liposome, or may be introduced directly through the skin, for example in a DNA vaccine. Alternatively, the nucleic acids encoding inhibitors are introduced into a cell ex vivo and the cells expressing the nucleic acids are introduced into a subject, e.g. by implantation procedures, to deliver the renin inhibitory agents in vivo.

Inhibitors of renin are known (see Fischli et al., Hypertension 18:22–31 (1991); Rahuel et al., J. Struct. Biol. 107:227–236 (1991); Badasso et al., J. Mol. Biol. 223:447–453 (1992); and Dhanaraj et al., Nature 357:466–472 (1992)). Monoclonal antibodies against human renin have been described (Galen et al., J. Clin. Invest. 74:723–735 (1984), and can be prepared according to methods well established in the art, e.g. by immunization of suitable host animals with renin. For descriptions of techniques for obtaining monoclonal antibodies see, e.g. the hybridoma technique of Kohler and Milstein (Nature 256:495–497 (1975)), the human B-cell hybridoma technique (Kosbor et al., Immunol. Today 4:72 (1983); Cole et al., Proc. Nat'l. Acad. Sci. USA, 80:2026–2030 (1983)) and the EBV-hybridoma technique (Cole et al., Monoclonal antibodies and Cancer Therapy, Alan R. Liss, Inc., pp. 77096 (1985)). Such antibodies may be of any immunoglobulin class including IgG, IgM, IgE, IgA, IgD and any subclass thereof. The hybridoma producing the monoclonal antibody may be cultivated in vitro or in vivo. Suitable host animals include, but are not limited to, rabbits, mice, rats, and goats. Various adjuvants may be used to increase the immunological response to the host animal, depending on the host species, including, but not limited to, Freund's (complete and incomplete), mineral gels such as aluminum hydroxide, surface active substances such as pluronic polyols, polyanions, peptides, oil emulsions, keyhole limpit, hemocyanin, dinitrophenol and potentially useful human adjuvants such as BCG (Bacille Calmette-Guerin) and Cornebacterium parvum. Antibodies as used herein includes non-human, chimeric (different species), humanized (see Borrebaeck, Antibody Engineering: A Practical Guide, W. H. Freeman and Co., New York, 1991), human and single-chain antibodies, as well as antibody fragments including but not limited to the F(ab')2 fragments that can be produced by pepsin digestion of antibody molecules and Fab fragments that can be generated by reducing disulfide bridges of the F(ab')2 fragments. Alternatively, Fab expression libraries may be constructed (Science 246:1275–1281 (1989)) to permit the rapid and easy identification of monoclonal Fab fragments having the desired specificity.

Also included within the scope of renin inhibitors of the invention are nucleic acids that include antisense oligonucleotides that block the expression of specific genes within cells by binding a complementary messenger RNA (mRNA) and preventing its translation (See review by Wagner, Nature 372:332–335 (1994); and Crooke and Lebleu, Antisense Research and Applications, CRC Press, Boca Raton (1993)). Gene inhibition may be measured by determining the degradation of the target RNA. Antisense DNA and RNA can be prepared by methods known in the art for synthesis of RNA including chemical synthesis such as solid phase phosphoramidite chemical synthesis or in vitro and in vivo transcription of DNA sequences encoding the anti sense RNA molecule. The DNA sequences may be incorporated into vectors with RNA polymerase promoters such as the T7 or SP6 polymerase promoters. Alternatively, antisense cDNA constructs that synthesize antisense RNA constitutively or inducibly can be introduced into cell lines. The potency of antisense oligonucleotides for inhibiting renin may be enhanced using various methods including 1) addition of polylysine (Leonetti et al., Bioconj. Biochem. 1:149–153 (1990)); 2) encapsulation into antibody targeted liposomes (Leonetti et al., Proc. Natl. Acad. Sci. USA 87:2448–2451 (1990) and Zelphati et al., Antisense Research and Development 3:323–338 (1993)); 3) nanoparticles (Rajaonarivony et al., J. Pharmaceutical Sciences 82:912–917 (1993) and Haensler and Szoka, Bioconj. Chem. 4:372–379 (1993)), 4) the use of cationic acid liposomes (Felgner et al., Proc. Natl. Acad. Sci. USA 84:7413–7417 (1987); Capaccioli et al., Biochem. Biophys. Res. Commun. 197:818–825 (1993); Boutorine and Kostina, Biochimie 75:35–41 (1993); Zhu et al., Science 261:209–211 (1993); Bennett et al., Molec. Pharmac. 41:1023–1033 (1992) and Wagner, Science 280:1510–1513 (1993)); and 5) Sendai virus derived liposomes (Compagnon et al., Exper. Cell Res. 200:333–338 (1992) and Morishita et al., Proc. Natl. Acad. Sci. USA 90:8474–8478 (1993)), to deliver the oligonucleotides into cells. Recent techniques for enhancing delivery include the conjugation of the antisense oligonucleotides to a fusogenic peptide, e.g. derived from an influenza hemagglutinin envelope protein (Bongartz et al., Nucleic Acids Res. 22(22):4681–4688 (1994)).

Additional suitable renin-specific inhibitory agents can be readily determined using methods known to the art to screen candidate agent molecules for binding to renin such as assays for detecting the ability of a candidate agent to block binding of radiolabeled human renin to human mesangial cells. Alternatively, candidate compounds may be tested for the ability to inhibit the renin-induced stimulation of TGFβ production by human mesangial cells measured by an enzyme-linked immunosorbent assay (ELISA), for example using the R & D Systems (Minneapolis, Minn.) TGFβ ELISA assay kit (Cat. No. DB 100) (for methods see, e.g. Uotila et al., J. Immunol. Methods 42:11 (1981)).

Suitable renin inhibitors can also be developed by known drug design methods, e.g. using structural analysis of the renin molecule employing methods established in the art, for example, using X-ray crystallography to analyze the structure of the complex formed by renin and one of its known inhibitors (see, e.g. Sielecki et al., supra; Rahuel et al., supra, Badasso et al., supra and Dhanaraj et al., supra.), and/or by modifying known renin antagonists i.e. "lead compounds," to obtain more potent inhibitors and compounds for different modes of administration (i.e. oral vs. intravenous) (see, e.g. Wexler et al., Amer. J. Hyper. 5:209S–220S (1992)-development of AII receptor antagonists from Losartantm). For such procedures large quantities of renin can be isolated and purified from mouse submaxillary glands and by recombinant DNA techniques (Vlahos et al., Biochem. Biophys. Res. Commun. 171:375–383 (1990)).

In another embodiment, the renin inhibitory agent is administered along with additional agents that directly or indirectly inhibit TGFβ production ("TGFβ inhibitory agents"), such as a TGFβ-specific inhibitory agent or an agent that blocks an alternative pathway of TGFβ production. For example, an indirect inhibitor would inhibit the synthesis or secretion of TGFβ or sequester it away from its target cells. Such inhibitors include, but are not limited to, inhibitors of Angiotensin Converting Enzyme ("ACE"), antagonists of the AII receptor such as Losartantm and Cozartm (Merck), and aldosterone inhibitor such as Spironolactonetm (Sigma Chemical Co., St. Louis, Mo., Product # S 3378) that would otherwise result in increased TGFβ production.

As used herein, a "TGFβ-specific inhibiting agent" means a protein or protein fragment containing TGFβ inhibiting activity, including agents that bind directly to or are a ligand for TGFβ which prevent it from binding to its receptors. Such agents include the decorin family of molecules, such as decorin, biglycan, fibromodulin and lumican (Krusius and Ruoslahti, Proc. Natl. Acad. Sci. USA 83:7638 (1986)), TGβ receptors such as betaglycan and endoglin, and soluble forms and fragments thereof having TGFβ-binding activity, antibodies and antibody fragments specific for TGFβ, TGFβ receptor antagonists and new TGFβ inhibitors developed using well known methods for drug discovery as described herein and in the art. A TGFβ-specific inhibiting agent also includes a nucleic acid encoding a particular TGFβ-specific inhibitory agent such as antisense TGFβ RNA or DNA.

The additional TGFβ inhibitory agent can also be introduced as nucleic acid together with or in sequence with the renin inhibitory nucleic acid.

As used herein "accumulation of excess extracellular matrix" means the deposition of extracellular matrix components including, collagen, fibronectin and proteoglycans in tissue to an extent that results in impairment of organ function and ultimately, organ failure as a result of fibrotic disease. "Reducing the accumulation of excess extracellular matrix" means preventing further deposition of extracellular matrix in tissue and/or decreasing the amount of already accumulated matrix in tissue.

A variety of diseases are characterized by excess accumulation of extracellular matrix (collagen, fibronectin and other matrix components). Such diseases include, for example, glomerulonephritis, adult or acute respiratory distress syndrome (ARDS), diabetes-associated pathologies such as diabetic kidney disease, fibrotic diseases of the liver, lung and post infarction cardiac fibrosis. Also included are fibrocytic diseases such as fibrosclerosis and fibrotic cancers such as cancers of the breast, uterus, pancreas or colon, and including fibroids, fibroma, fibroadenomas and fibrosarcomas.

There are also a number of medical conditions associated with an excess accumulation of extracellular matrix involving increased collagen, fibronectin and other matrix components. Such conditions include, for example, post myocardial infarction, cardiac fibrosis and post-angioplasty restenosis and renal interstitial fibrosis, excessive scarring such as keloid scars and scars resulting from injury, burns or surgery.

The diseases and conditions disclosed herein as associated with TGFβ-induced excess accumulation of extracellular matrix are sufficiently similar in pathology to be included in the general category known as "fibrotic diseases." As discussed, supra, it is known that TGFβ is indicated in the causation of fibrotic diseases. During normal tissue repair, TGFβ production is increased to stimulate the process of repair. When repair is complete, TGFβ production is reduced. If not reduced following normal tissue repair, the increased TGFβ production can result in the development of excess extracellular matrix accumulation and fibrotic disease. Thus, repeated tissue injury or a defect in TGFβ regulation leading to sustained TGFβ production results in excess accumulation of extracellular matrix.

Gene Therapy Methods

In one embodiment of the invention, nucleic acid encoding a renin-inhibitory agent is introduced into cells in a subject to express the renin-inhibiting agent and suppress TGFβ upregulation. Gene transfer into cells of nucleic acid encoding TGFβ inhibitory agents for administration with the renin inhibitory agent is also contemplated.

For gene transfer, the key steps are 1) to select the mode of delivery, e.g. a proper vector for delivery of the inhibitor genes to the subject, 2) administer the nucleic acid to the subject; and 3) achieve appropriate expression of the transferred gene for satisfactory durations. Methods for gene transfer are known in the art. The method described below are merely for purposes of illustration and are typical of those that can be used to practice the invention. However, other procedures may also be employed, as is understood in the art. Most of the techniques to construct delivery vehicles such as vectors and the like are widely practices in the art, and most practitioners are familiar with the standard resource materials which describe specific conditions, reagents and procedures. The following paragraphs may serve as a guideline.

Techniques for nucleic acid manipulation are well known. (See, e.g. Annual Rev. of Biochem. 61:131–156 (1992)). Reagents useful in applying such techniques, such as restriction enzymes and the like, are widely known in the art and commercially available from a number of vendors.

Large amounts of the nucleic acid sequences encoding the renin inhibitors and the TGFβ inhibitors may be obtained using well-established procedures for molecular cloning and replication of the vector or plasmid carrying the sequences in a suitable host cell. DNA sequences encoding a specific renin inhibitor can be assembled from cDNA fragments and oligonucleotide linkers, or from a series of oligonucleotides to provide a synthetic renin inhibitor agent gene which can be expressed. Such sequences are preferably provided in an open reading frame uninterrupted by internal non-translated sequences or introns, which are typically present in eukaryotic genes. Genomic DNA containing the relevant sequences can also be used. Sequences of non-translated DNA may be present 5' to 3' from the open reading frame, where such sequences do not interfere with manipulation or expression of the coding regions. Either complete gene sequences or partial sequences encoding the desired renin inhibitors can be employed.

The nucleic acid sequences encoding the renin or TGFβ inhibitors can also be produced in part or in total by chemical synthesis, e.g. by the phosphoramidite method described by Beaucage and Carruthers, Tetra Letts. 22:1859–1862 (1981) or the triester method (Matteucci et al., J. Am. Chem. Soc. 103:3185 (1981) and may be performed on commercial automated oligonucleotide synthesizers. A double-stranded fragment may be obtained from the single-stranded product of chemical synthesis either by synthesizing the complementary strand and annealing the strand together under appropriate conditions, or by synthesizing the complementary strand using DNA polymerase with an appropriate primer sequence.

The natural or synthetic nucleic acid coding for the inhibitors for expression in a subject may be incorporated into vectors capable of introduction into and replication in the subject. In general, nucleic acid encoding the selected inhibitor molecules is inserted using standard recombinant techniques into a vector containing appropriate transcription and translation control sequences, including initiation sequences operably linked to the gene sequence to result in expression of the recombinant genes in the recipient host cells. "Operably linked" means that the components are in a physical and functional relationship permitting them to function in their intended manner. For example, a promoter is operably linked to a coding sequence if the promoter effects its transcription or expression.

Sequences encoding selected renin and/or TGFβ inhibitors will include at least a portion of the coding sequence sufficient to provide anti-renin or anti-TGFβ activity in the expressed molecule. For example, in the case of a renin inhibitor, a portion of the coding sequence that enables the inhibitor to bind to renin can be used. Methods for determining such portions or "domains" including binding domains of molecules, are known in the art (See, e.g., Linsley et al., Proc. Natl. Acad. Sci. USA 87:5031–5035 (1990)).

The selected nucleic acid sequences are inserted into a single vector or separate vectors. More than one gene encoding a selected inhibitor, or portion thereof, may be inserted into a single vector or into separate vectors for introduction into the host cells. Alternatively, these sequences can be administered as naked nucleic acid sequences or as part of a complex with other molecules, e.g. liposomes.

A variety of expression vectors and gene transfer methods useful for obtaining expression of a renin-specific inhibitory agent in recipient cells are well known in the art, and can be constructed using standard ligation and restriction techniques (see, for example, Sambrook et al., Molecular Cloning: A Laboratory Manual, Cold Spring Harbor Laboratory Press, 1989; Maniatis et al., Molecular Cloning: A Laboratory Manual, Cold Spring Harbor, N.Y. (1982), Kriegler, Gene Transfer and Expression: A Laboratory Manual (W. H. Freeman and Co., New York, N.Y. 1990) and Wu, Methods in Enzymol. (Academic Press, New York, N.Y. 1993), each of which is incorporated by reference herein). The choice of vector or method depends on several factors such as the particular renin inhibitory agent.

Suitable vectors may be plasmid or viral vectors (Kaufman, in Gene Expression Technology, Goeddel (Ed.) (1991)) including baculoviruses, adenoviruses, poxviruses (Moss, Current Opin. Biotech. 3:518–522 (1993)), retrotransposon vectors (Cook et al., Bio/Technology 9:748–751 (1991) and Chakraborty et al., FASEB J. 7:971–977 (1993)) adeno-associated viruses (AAV) (Yei et al., Gene Therapy 1:192–200 (1994) and Smith et al., Nat. Genet. 5:397–402 (1993)), herpes virus and retrovirus vectors (Price et al., Proc. Natl. Acad. Sci. USA 84:156–160 (1987); Naviaux and Verma, Current Opinion in Biotechnol. 3:540–547 (1992); Hodgson and Chakraborty, Curr. Opin. Thera. Patients 3:223–235 (1993)) such as the MMLV based replication incompetent vector pMV-7 (Kirschmeier et al., DNA 7:219–225 (1988)), as well as human and yeast artificial chromosomes (HACs and YACs) (Huxley, Gene Therapy 1:7–12 (1994) and Huxley et al., Bio/Technology 12:586–590 (1994)). Plasmid expression vectors include plasmids including pBR322, pUC or Bluescripttm (Stratagene, San Diego, Calif.).

Vectors containing the nucleic acid encoding the inhibitory agents are preferably recombinant expression vectors in which high levels of gene expression may occur, and which contain appropriate regulatory sequences for transcription and translation of the inserted nucleic acid sequence. Regulatory sequences refer to those sequences normally associated (e.g. within 50 kb) of the coding region of a locus which affect the expression of the gene (including transcription, translation, splicing, stability or the like, of the messenger RNA). A transcriptional regulatory region encompasses all the elements necessary for transcription, including the promoter sequence, enhancer sequence and transcription factor binding sites. Regulatory sequences also include, inter alia, splice sites and polyadenylation sites. An internal ribosome entry site (IRES) sequence may be placed between recombinant coding sequences to permit expression of more than one coding sequence with a single promoter.

Transcriptional control regions include: the SV40 early promoter region, the cytomegalovirus (CMV) promoter (human CMV IE94 promoter region (Boshart et al., Cell 41:521–530 (1985)); the promoter contained in the 3' long terminal repeat of Rous Sarcoma Virus or other retroviruses; the herpes thymidine kinase promoter; the regulatory sequences of the methallothionein gene; regions from the human IL-2 gene (Fujita et al., Cell 46:401–407 (1986)); regions from the human IFN gene (Ciccarone et al., J. Immunol. 144:725–730 (1990); regions from the human IFN gene (Shoemaker et al., Proc. Natl. Acad. Sci. USA 87:9650–9654 (1990); regions from the human IL-4 gene (Arai et al., J. Immunol. 142:274–282 (1989)); regions from the human lymphotoxin gene (Nedwin et al., Nucl. Acids. Res. 13:6361–6373 (1985)); regions from the human granulocyte-macrophage CSF gene (GM-CSF) (Miyatake et al., EMBO J. 4:2561–2568 (1985)) and others. When viral vectors are used, recombinant-coding sequences may be positioned in the vector so that their expression is regulated by regulatory sequences such as promoters naturally residing in the viral vector.

Operational elements for obtaining expression may include leader sequences, termination codons and other sequences needed or preferred for the appropriate transcription and translation of the inserted nucleic acid sequences. Secretion signals may also be included whether from the native inhibitor or from other secreted polypeptides, which permit the molecule to enter cell membranes and attain a functional conformation. It will be understood by one skilled in the art that the correction type and combination of expression control elements depends on the recipient host cells chosen to express the molecules ex vivo. The expression vector should contain additional elements needed for the transfer and subsequent replication of the expression vector containing the inserted nucleic acid sequences in the host cells. Examples of such elements include, but are not limited to, origins of replication and selectable markers. Additionally, elements such as enhancer sequences, for example CMV enhancer sequences, may be used to increase the level of therapeutic gene expression (Armelor. Proc. Natl. Acad. Sci. USA 70:2702 (1973)).

The vector may contain at least one positive marker that enables the selection of cells carrying the inserted nucleic acids. The selectable molecule may be a gene which, upon introduction into the host cell, expresses a dominant phenotype permitting positive selection of cells carrying the gene ex vivo. Genes of this type are known in the art and include, for example, drug resistance genes such as hygromycin-B phosphotransferase (hph) which confers resistance to the antibiotic G418; the aminoglycoside phosphotransferase gene (neo or aph) from Tn5 which codes for resistance to the antibiotic G418; the dihydrofolate reductase (DHRF) gene; the adenosine deaminase gene (ADA) and the multi-drug resistance (MDR) gene.

Recombinant viral vectors are introduced into host cells using standard techniques. Infection techniques have been developed which use recombinant infectious virus particles for gene delivery into cells. Viral vectors used in this way include vectors derived from simian virus 40 (SV40; Karlsson et al., Proc. Natl. Acad. Sci. USA 82:158 (1985)); adenoviruses (Karlsson et al., EMBO J. 5:2377 (1986)); vaccinia virus (Moss et al., Vaccine 6:161–3 (1988)); and retroviruses (Coffin, in Weiss et al. (Eds.), RNA Tumor Viruses, $2^{nd}$ Ed., Vol. 2, Cold Spring Laboratory, N.Y., pp. 17–71 (1985)).

Nonreplicating viral vectors can be produced in packaging cell lines which produce virus particles which are infectious but replication defective, rendering them useful vectors for introduction of nucleic acid into a cell lacking complementary genetic information enabling encapsidation (Mann et al., Cell 33:153 (1983); Miller and Buttimore, Mol. Cell. Biol. 6:2895 (PA317, ATCC CRL9078). Packaging cell lines which contain amphotrophic packaging genes able to transduce cells of human and other species origin are preferred.

Vectors containing the inserted inhibitor genes or coding sequences are introduced into host cell using standard methods of transfection including electroporation, liposomal preparations, Ca-PH-DNA gels, DEAE-dextran, nucleic acid particle "guns" and other suitable methods.

In additional to various vectors including viral vectors, other delivery systems may be used including, but not limited to, microinjection (DePamphilis et al., BioTechnique 6:662–680 (1988)); liposomal mediated transfection (Feigner et al., Proc. Natl. Acad. Sci. USA 84:7413–7417 (1987); Feigner and Holm, Focus 11:21–25 (1989) and Feigner et al., Proc. West. Pharmacol. Soc. 32:115–121 (1989)); use of naked or particle mediated DNA transfer and other methods known in the art. Recently, cationic liposomes have been used to enhance transfection (Feigner et al., Nature 349:351 (1991); Zhu et al., Science 261:209 (1993)).

Suitable host cells for gene transfer consist of vertebrate cells such as fibroblasts, keratinocytes, muscle cells, mesangial cells (see, Kitamura et al., Kidney Int. 48:1747–1757 (1995)), and any other suitable host cell including so-called universal host cells, i.e. cells obtained from a different donor than the recipient subject but genetically modified to inhibit rejection by the subject. Autologous cells are preferred, but heterologous cells are encompassed within the scope of the invention.

Expression of the selected inhibitor genes after introduction into the host cells is confirmed by assaying for the ability of the supernatant to inhibit the production of TGFβ. For example, radiolabelled human renin can be added to cultured human mesangial cells in the presence of the inhibitor transfected host cells. Inhibition of binding of the labeled renin to the cells indicates expression of anti-renin compound. Alternatively, an ELISA can be used to assay for inhibition of TGFβ production by the target (mesangial) cells, or to detect levels of fibronectin or PAI-1 as an indicator of effects on TGFβ expression. Yet another technique is to confirm expression of renin-inhibitory molecules by detecting binding of labeled anti-inhibitor antibodies to the mesangial cells using Fluorescent Activated Cell Sorting (FACS) or ELISA.

Administration of Inhibitors

The compositions containing renin inhibitors and renin inhibitors with additional TGFβ inhibitors are suspended in a physiologically compatible pharmaceutical carrier, such as physiological saline, phosphate-buffered saline, or the like to form a physiologically acceptable aqueous pharmaceutical composition for administration to a subject. Parenteral vehicles include sodium chloride solution, Ringer's desctrose, dextrose and sodium chloride and lactated Ringer's solution. Other substances may be added a desired, such as antimicrobials.

Modes of administration of the inhibitors are those known in the art for therapeutic agents and include parenteral, for example, intravenous (e.g. for antibody inhibitors), intraperitoneal, intramuscular, intradermal, and epidermal including subcutaneous and intradermal, oral (e.g. small molecule renin and TGFβ antagonists), or applied to mucosal surfaces, e.g. by intranasal administration using inhalation of aerosol suspensions, and by implanting to muscle or other tissue in the subject (e.g. for gene transfer of nucleic acid expressing renin and/or TGFβ inhibitors). Suppositories and topical preparations are also contemplated.

The inhibitors are introduced in amounts sufficient to prevent or reduce accumulation of extracellular matrix in susceptible tissues including, but not limited to, lung and kidney tissue. Before or after administration, if necessary to prevent or inhibit the subject's immune response to the vehicles carrying the inhibitors, immunosuppressant agents may be used. Alternatively, the vehicles carrying the inhibitors can be encapsulated.

The most effective mode of administration and dosage regimen for the inhibitors in the methods of the present invention depend on the severity of the accumulation of extracellular matrix and fibrotic disease, the subject's health, previous medical history, age, weight, height, sex and response to treatment and the judgment of the treating physician. Therefore, the amount of inhibitors to be administered, as well as the number and timing of subsequent administrations are determined by a medical professional conducting therapy based on the response of the individual subject. Initially, such parameters are readily determined by skilled practitioners using appropriate testing in animal models for safety and efficacy, and in human subjects during clinical trials of candidate therapeutic inhibitor formulations. Suitable animal models of human fibrotic disease are known (see, e.g. Border and Noble, New Eng. J. Med. 331:1286–1292 (1994), incorporated by reference herein).

After administration, the efficacy of the therapy using the inhibitors is assessed by various methods including biopsy of kidney, lung or liver or other tissue to detect the amount of extracellular matrix accumulating. A decrease in the amount or expansion of ECM in the tissue will indicate the desired therapeutic response in the subject. Preferably, a non-invasive procedure is used to detect changes in TGFβ activity. For example, TGFβ could be measured in plasma samples taken before and after treatment with an inhibitor (see, Eltayeb et al., J. Am. Soc. Nephrol. 8:110A (1997)), and biopsy tissue can be used to individually isolate diseased glomeruli which are then used for RNA isolation. mRNA transcripts for TGFβ, and extracellular matrix components (e.g. collagen) are then determined using reverse transcriptase-polymerase chain reaction (RT-PCR) (Peten et al., J. Exp. Med. 176:1571–1576 (1992)).

The therapeutic effects of the invention result from a reduction in the TGFβ-induced accumulation of extracellular matrix in tissue and increased degradation of ECM over time after administration of renin inhibitors or renin inhibitors in combination with additional TGFβ inhibitors.

Advantages of the Invention

The invention provides improved therapy of tissue impaired by accumulation of extracellular matrix by reducing TGFβ production resulting from multiple biological pathways to effectively inhibit the TGFβ induced component of extracellular matrix.

The following examples are presented to demonstrate the methods of the present invention and to assist one of ordinary skill in using the same. The examples are not intended in any way to otherwise limit the scope of the disclosure of the protection granted by Letters Patent granted hereon.

EXAMPLE 1

Demonstration that Renin Upregulates TGFβ in Human Mesangial Cells

Normal fetal human mesangial cells (Clonetics Corp., Clonetics, Walkersville, Md.) passaged 5 to 8 times, were plated (3,000 cell/cm$^2$) in 12 well plates in 2 ml of medium (Mesangial Basal Medium (Clonetics Corp.) containing 5% FCS, 10 μg/ml penicillin and 100 μg/ml streptomycin) and allowed to grow to confluence for 48 hours at 37° C., 5% $CO_2$. Cultures were washed three times using sterile phosphate buffered saline at room temperature and then 2 ml/well of serum free MBM medium to induce quiescence. After 48 hours, the serum-free medium was removed and 2 ml/well of fresh serum-free medium was added. Human recombinant renin (Hoffman-La Roche Ltd., Basel, Switzerland) in concentrations from $10^{-6}$ to $10^{-12}$ M was added to each well. A blank and 5 ng/ml of TGFβ (R & D Systems, Minneapolis, Minn.) were used as controls. Cells and supernatants were harvested by centrifugation after 24 hrs of culture and frozen at −70° C. until analysis. The total production and release of TGFβ into the culture supernatant was measured using an ELISA kit (R & D Systems). Induction of PAI-1 and fibronectin in the supernatant are also measured using anti-PAI-1 and anti-fibronectin antibodies in an ELISA to provide further confirmation of the inhibition of TGFβ. TGFβ, fibronectin and PAI-1 mRNA are measured using semi-quantitative RT-PCR.

(1) Determination of Dose Dependency of Renin Induction of TGFβ

As shown in FIG. 1, renin increases the TGFβ production by cultured human mesangial cells in a dose-dependent manner.

EXAMPLE 2
Demonstration of the Effect of Inhibiting Renin on TGFβ Production by Human Mesangial Cells Renin inhibitor Ro42-5892 (Hoffman-LaRoche, Basel, Switzerland), Losartantm (Merck Pharmaceuticals, West Point, Pa.), Enalapril™ (Sigma Chemical Co., St. Louis, Mo., Prod. No. E6888), or TGFβ 1 neutralizing antibody (R & D Systems) were added in the amounts indicated below to separate wells in triplicate to block the renin cascade at different sites after stimulation by renin:

$10^{-5}$ M Renin Inhibitor R042-5892 (Hoffman-LaRoche)

30 ng/ml Anti-TGFβ 1 antibody (R & D Systems, # AB 101 NA)

30 ng/ml Chicken IgG (control for anti-TGFβ 1 antibody, R & D Systems, # AB 101 C)

$10^{-5}$ M Enalapril™ (Sigma Chemical Co., St. Louis, Mo.)

$10^{-5}$ M Losartan™ (Merck Pharmaceuticals, West Point, Pa.)

These inhibitors were added at zero time with $10^{-7}$ M human recombinant renin (Hoffman-LaRoche).

Figure 2:
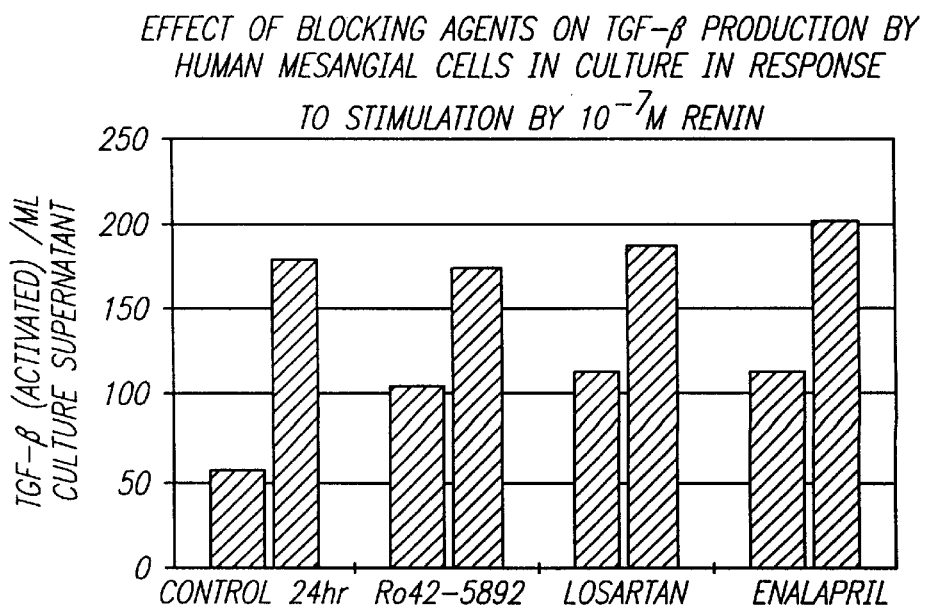
FIG. 2 is a bar graph showing the effect of blocking agents on TGFβ production by human mesangial cells in response to renin, as described in Example II, infra.

As shown in FIG. 2, use of inhibitors that block renin's action to increase Angiotensin II, i.e. blocking Angiotensin I production from Angiotensinogen (Ro 42-5892), blocking Angiotensin I conversion to Angiotensin II (Enalapril™) and blocking binding of Angiotensin II to its type I receptor (Losartan™), does not reduce the renin-induced increase in TGFβ production. These results demonstrate for the first time an alternative pathway in which TGFβ production is stimulated by renin.

EXAMPLE 3
Demonstration of Inhibition of TGFβ by Blocking Renin in Vivo in the Presence of an Anti-Fibrotic Drug In this example, a known fibrotic disease drug, Enalapril™ which inhibits the production of Angiotensin II, is combined with an inhibitor of renin, antisense renin oligonucleotide, to obtain an enhanced therapeutic effect on fibrotic disease in an animal model.

Rats are administered Enalapril™ in their drinking water prior to anti-thymocyte serum injection, e.g. three (3) days prior to injection. Anti-thymocyte antibody, e.g. OX-7, is injected intravenously into the rats at day three to produce fibrotic disease. (Bagchus et l., Lab. Invest. 55:680–687 (1986)). Renin antisense oligonucleotides are administered one hour following administration of OX-7 by introducing the oligonucleotides into a suitable vehicle, such as HVJ liposomes, and injecting the formulations into the left renal artery of Sprague Dawley rats as described for renin genes by Arai et al., Biochem. And Biophys. Res. Comm. 206(2):525–532 (1995), incorporated by reference herein. A control consisting of nonsense encoding oligonucleotides (e.g. derived from the renin antisense gene sequence) is also injected into the left renal artery of additional rats. The renin antisense localizes in the juxtaglomerular apparatus of the glomerulus where renin is produced blocking renin production.

Animals are sacrificed on day 7 and kidney tissue samples are taken for analysis of levels of TGFβ in the glomeruli. Glomeruli are sieved individually from each rat and placed in culture in suitable medium for three days. At the end of culture, culture supernatant is harvested by centrifugation and TGFβ, fibronectin and PAI-1 production are determined as markers of fibrotic renal disease severity. Other glomeruli are pooled and used to isolate RNA. RNA is used by standard methods to quantitate expression of mRNAs of interest, including TGFβ, fibronectin and collagens.

Glomeruli are also examined histologically for phenotypical changes, e.g. changes resulting from deposition for ECM. Phenotypic changes are associated with pathological alteration of glomeruli indicative of fibrotic disease. Such changes include expansion of extracellular matrix in the mesangial area of the kidney in animal models and the presence of activated mesangial cells which have acquired the characteristics of fibroblasts, e.g. expressing β-smooth muscle actin and interstitial collagen, indicating progressive glomerular injury (Johnson et al., J. Am. Soc. Nephrol. 2:S190–S197 (1992)). Tissue for light microscopy is fixed in formaldehyde, then dehydrated in graded ethanol and embedded in paraffin. Sections are cut at 3 μm thickness and are stained with the periodic Schiff reagent. The paraformaldehyde-fixed renal section of the rats are also incubated with mouse anti-human renin monoclonal antibody (Kaiichi Radioisotope Labs, Ltd., Tokyo, Japan), mouse anti-smooth muscle actin monoclonal antibody (Immunotech S. A. (Marseille, France) and rabbit anti-collagen antibodies (Chemicon, Temicula, Calif., prod. No. AB755). The sections are further processed using Vectastain ABC Kit (Vector Laboratories, Inc., Burlingame, Calif.). Results of antibody binding indicate the extent of glomerular injury and the effects of inhibition of renin on such injury.

EXAMPLE 4
Demonstration that Renin Upregulates TGFβ in Human Mesangial Cells

Primary cultures of adult human mesangial cells were grown from human nephrectomy tissues using standard methods. Cells were passaged 4–7 times and then plated (3,000 cell/cm$^2$) in 12 well plates in 2 ml of medium (Mesangial Basal Medium (Clonetics Corp.) containing 5% FCS, 10 μg/ml penicillin and 100 μg/ml streptomycin) and allowed to grow to 70% confluency for 48 hours at 37° C., 5% $CO_2$. Cultures were washed three times using sterile phosphate buffered saline at room temperature and then 2 ml/well of serum free MBM medium to induce quiescence. After 48 hours, the serum-free medium was removed and 2 ml/well of fresh serum-free medium was added for 24 hours. Human recombinant renin (HrRenin, Hoffman-La Roche Ltd., Basel, Switzerland) in concentrations from $10^{-6}$ to $10^{-12}$ M was added to each well for 24 hours. A blank (no HrRenin) was used as a control. Cells and supernatants were harvested by centrifugation after 24 hrs of culture and frozen at −70° C. until analysis.

The total production and release of TGFβ into the culture supernatant was measured using an ELISA kit (R & D Systems). Induction of the matrix protein fibronectin (Fn) in the supernatant was measured using anti-fibronectin antibodies in an ELISA to provide further confirmation of induction of TGFβ. Renin-induced induction of TGFβ, fibronectin and PAI-1 mRNA were measured over time using semi-quantitative RT-PCR in a multiplex system where multiple cDNAs are amplified simultaneously according to Dostal et al., Anal. Biochem. 223:239–250 (1994), incorporated by reference herein Determinations were done in triplicate mesangial cell cultures.

(1) Determination of Dose Dependency of Renin Induction of TGFβ

Figure 3A:
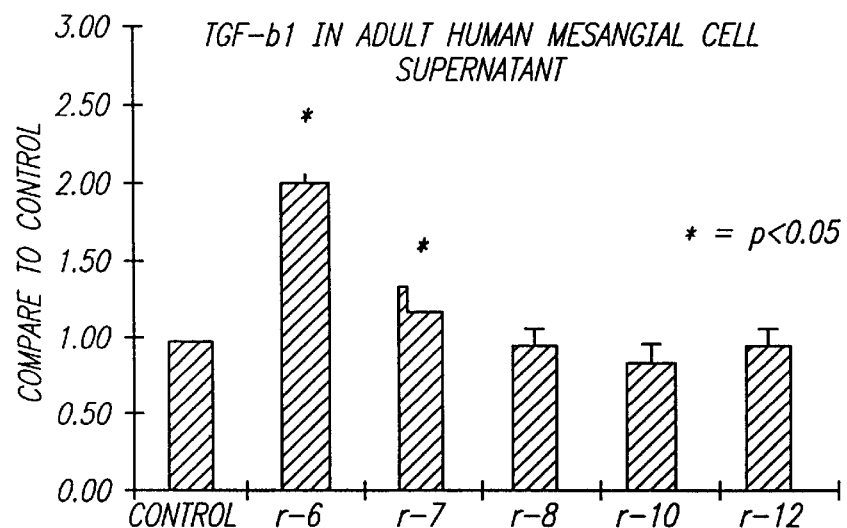
FIGS. 3A and 3B are bar graphs showing dose dependent increases in TGFβ (FIG. 3A) and Fn production (FIG. 3B) with increases in HrRenin as described in Example IV, infra.
Figure 3B:
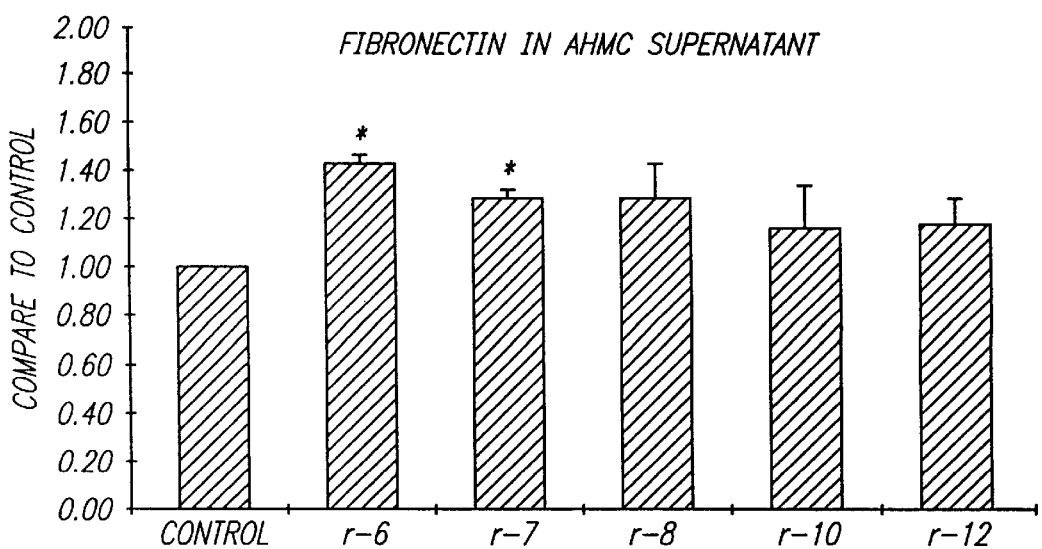
Figure 5A:
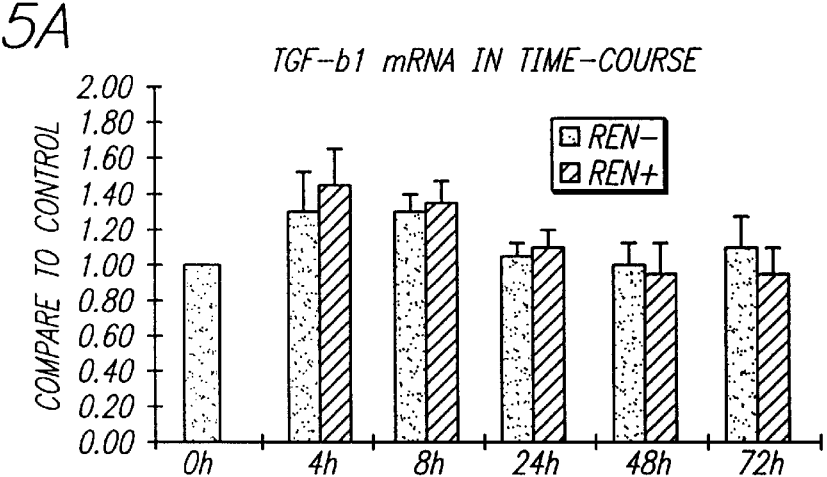
FIGS. 5A–C are bar graphs showing renin-induced increases in TGFβ, PAI-1 and Fn mRNAs over time as described in Example IV, infra.
Figure 5B:
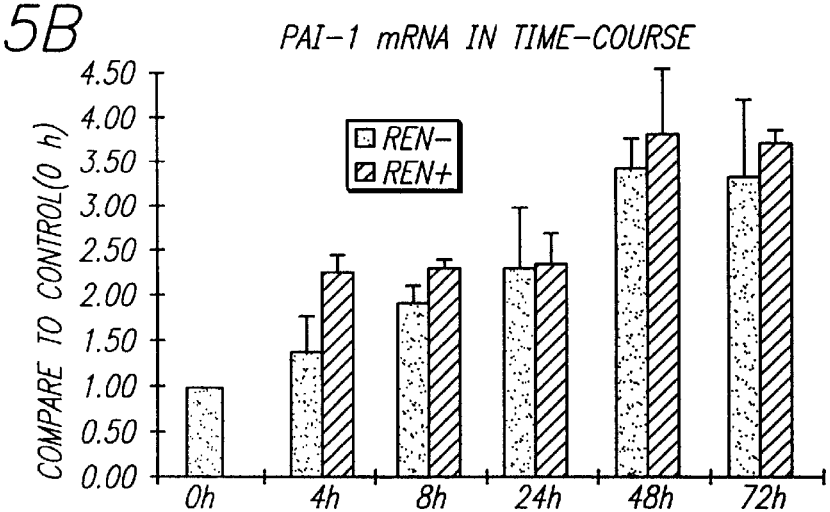
Figure 5C:
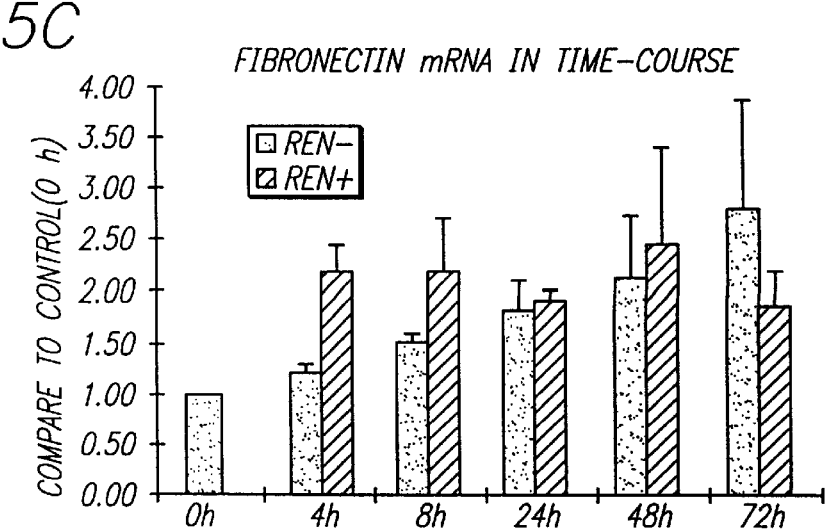

As shown in FIG. 3, statistically significant (p<0.05) dose dependent increases in TGFβ (FIG. 3A) and Fn production (FIG. 3B) were observed, peaking with 2- and 4-fold increases at $10^{-6}$M HrRenin, respectively. Time course experiments using $10^{-7}$M HrRenin revealed significant increases in TGFβ and Fn production at 24 and 48 hours (p<0.03) (FIGS. 4A and B). As shown in FIGS. 5A–C, renin-induced increases in TGFβ, PAI-1 and Fn mRNAs peaked at 4 hours with increases from 1.5- to 2-fold.

(2) Demonstration that Renin Upregulation of TGFβ is not Mediated through Renin Enzymatic Activity or Angiotensin II Renin inhibitor Ro42-5892 (Hoffman-LaRoche, Basel, Switzerland), Losartantm (Merck Pharmaceuticals, West Point, Pa.), Enalapriltm (Sigma Chemical Co., St. Louis, Mo., Prod. No. E6888), or TGFβ 1 neutralizing antibody (R & D Systems) were added in the amounts indicated below to separate wells in triplicate to block the renin cascade at different sites after stimulation by renin:

$10^{-5}$ M Renin Inhibitor R042-5892 (Hoffman-LaRoche)

$10^{-5}$ M Enalapril™ (Sigma Chemical Co., St. Louis, Mo.)

$10^{-5}$ M Losartan™ (Merck Pharmaceuticals, West Point, Pa.)

Controls included neutralizing antibody to TGFβ (ATG) and control IgG (TgG)

These inhibitors were added at zero time with $10^{-7}$ M human recombinant renin (Hoffman-LaRoche).

Figure 6:
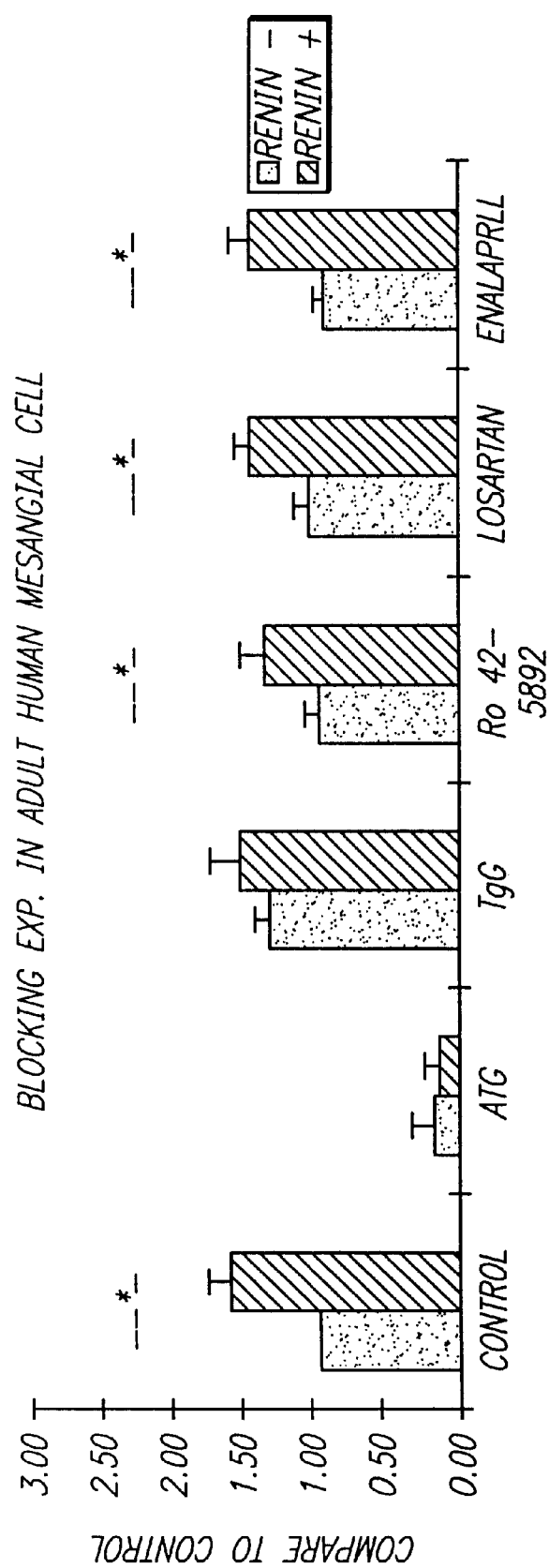
FIG. 6 is a bar graph showing the results of inhibitors that block renin's action to increase Angiotensin II, on the renin-induced increase in TGFβ production in adult human mesangial cells as described in Example IV, infra.

As shown in FIG. 6, use of inhibitors that block renin's action to increase Angiotensin II, i.e. blocking Angiotensin I production from Angiotensinogen (RO 42-5892), blocking Angiotensin I conversion to Angiotensin II (Enalapril™) and blocking binding of Angiotensin II to its type I receptor (Losartan™), does not reduce the renin-induced increase in TGFβ production.

These results provide additional evidence that renin upregulates TGFβ production by human mesangial cells through a mechanism which is independent of renin's enzymatic action to convert angiotensin to Angiotensin I, and independent of Angiotensin II generation. These results may have profound implications for progression of fibrotic renal disease, particularly in states of high plasma renin as are observed with therapeutic Angiotensin II blockade. Thus, the use of therapeutic agents such as Enalapril™ or Losartan™ for Angiotensin blockade may not be optimal as treatment agents because of resulting high renin levels, preventing a therapeutic reduction in TGFβ. In addition, antagonists developed to block the site on renin that acts in the Angiotensin II pathway, would not be expected to block the action of renin that is independent of this pathway. Therefore, effective therapy of fibrotic diseases must take these multiple pathways for TGFβ increase into consideration. The present invention provides methods to counteract the effects of renin on upregulation of TGFβ and thus approach an effective therapy of diseases associated with overexpression of TGFβ.

Various publications are cited herein that are hereby incorporated by reference in their entirety.

As will be apparent to those skilled in the art in which the invention is addressed, the present invention may be embodied in forms other than those specifically disclosed without departing from the spirit or potential characteristics of the invention. Particular embodiments of the present invention described above are therefore to be considered in all respects as illustrative and not restrictive. The scope of the invention is as set forth in the appended claims and equivalents thereof rather than being limited to the examples contained in the foregoing description.

We claim:

1. A method for inhibiting the Angiotensin-II independent, renin-induced production of TGFβ by cells that produce and secrete TGFβ comprising inhibiting the activity of renin by contacting renin or its receptor with a renin inhibitory agent, selected from the group consisting of anti-renin antibodies, peptide inhibitors of renin and renin receptor ligands, in an amount effective to reduce the production of TGFβ by cells that produce and secrete TGFβ.

2. A method for reducing TGFβ-induced accumulation of extracellular matrix by cells that produce and secrete TGFβ comprising inhibiting renin by contacting renin or its receptor with a renin inhibitory agent, selected from the group consisting of anti-renin antibodies, small molecule antagonists of renin and renin receptor ligands, in an amount effective to reduce the Angiotnesin-II independent renin-induced production of TGFβ by cells that produce and secrete TGFβ, thereby reducing accumulation of extracellular matrix.

3. A method for reducing the accumulation of excess extracellular matrix induced by TGFβ produced by cells comprising contacting renin with a renin inhibitory agent, selected from the group consisting of anti-renin antibodies, peptide inhibitors of renin and renin receptor ligands, that inhibits the Angiotensin-II independent renin-induced production of TGFβ, and at least one additional agent that inhibits the activity of TGFβ, in amounts effective to reduce the activity of TGFβ by said cells, thereby reducing accumulation of extracellular matrix.

4. The method of claim 3 wherein said additional inhibitory agent is selected from the group consisting of an angiotension II inhibitory agent and an aldosterone inhibitory agent.

5. The method of claim 3, wherein said additional inhibitory agent is an anti-TGFβ agent selected from the group consisting of an anti-TGFβ antibody, a molecule from the decorin family, and a ligand for the TGFβ receptor.

6. A method for reducing excess accumulation of extracellular matrix induced by TGFβ in tissues, comprising administering to said tissues a combination of pharmaceutical agents selected from the group consisting of an inhibitor of renin, selected from the group consisting of anti-renin antibodies, peptide inhibitors of renin, and renin receptor ligands, an inhibitor of angiotensin II activity and an inhibitor of aldosterone activity, thereby reducing the excess accumulation of extracellular matrix in said tissues.

7. The method of claim 6, further comprising administering an additional TGFb inhibitory agent, wherein said agent inhibits the activity of TGFβ.

8. The method of claim 1 further comprising administering an additional anti-TGFβ inhibitory agent, wherein said agent inhibits the activity of TGFβ.

9. The method of claim 8, wherein said additional agent is selected from the group consisting of an angiotensin II inhibitory agent, an aldosterone inhibitory agent, an anti-TGFβ antibody, a molecule from the decorin family and a ligand for the TGFβ receptor.

* * * * *